United States Patent
Yamada

(10) Patent No.: US 6,614,044 B2
(45) Date of Patent: Sep. 2, 2003

(54) IMAGE SIGNAL GENERATING METHOD, APPARATUS AND PROGRAM

(75) Inventor: Masahiko Yamada, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 176 days.

(21) Appl. No.: 09/939,632

(22) Filed: Aug. 28, 2001

(65) Prior Publication Data

US 2002/0024027 A1 Feb. 28, 2002

(30) Foreign Application Priority Data

Aug. 28, 2000 (JP) ........................................ 2000-257668

(51) Int. Cl.$^7$ ............................................... G03B 42/08
(52) U.S. Cl. ........................................ 250/584; 250/581
(58) Field of Search ................................. 250/584, 581, 250/580, 484.4, 483.1

(56) References Cited

U.S. PATENT DOCUMENTS

| | | | |
|---|---|---|---|
| 4,258,264 A | 3/1981 | Kotera et al. | 250/484 |
| 4,276,473 A | 6/1981 | Kato et al. | 250/327.1 |
| 4,315,318 A | 2/1982 | Kato et al. | 364/515 |
| 5,028,784 A * | 7/1991 | Arakawa et al. | 250/327.2 |
| 2002/0040972 A1 * | 4/2002 | Arakawa | 250/586 |
| 2002/0180877 A1 * | 12/2002 | Kikuchi | 348/315 |
| 2002/0196901 A1 * | 12/2002 | Inoue | 378/154 |
| 2003/0016854 A1 * | 1/2003 | Inoue | 382/132 |

FOREIGN PATENT DOCUMENTS

| | | | |
|---|---|---|---|
| JP | 55-12429 | 1/1980 | G01T/1/10 |
| JP | 55-116340 | 9/1980 | A61B/6/00 |
| JP | 55-163472 | 12/1980 | G01T/1/29 |
| JP | 56-11395 | 2/1981 | G21K/4/00 |
| JP | 56-164645 | 12/1981 | H04J/1/10 |

OTHER PUBLICATIONS

Abstract 56011395, Feb. 4, 1981.
Abstract 56–164645, Dec. 17, 1981.

* cited by examiner

Primary Examiner—David Porta
Assistant Examiner—Christine Sung
(74) Attorney, Agent, or Firm—Sughrue Mion, PLLC

(57) ABSTRACT

An image free from aliasing or moiré is obtained when a spatial frequency of a repeated pattern such as a grid pattern is smaller than a spatial frequency required for image information. In one embodiment, digital image data S1 is first obtained by reading a radiation image from a storage-type phosphor sheet storing the radiation image taken using a grid of 4 bars/mm, the reading being performed at sampling intervals of 20 cycles/mm. Image data S1 contains the grid pattern component at 4 cycles/mm, and harmonics components of the grid pattern at 8, 12, 16 and 20 cycles/mm. The harmonics components are removed by filtering processing, and the image data is sampled down to one half to obtain an image data with a Nyquist frequency of 10 cycles/mm. Further filtering processing and sub-sampling processing are performed to obtain an image data with a Nyquist frequency of 5 cycles/mm.

9 Claims, 8 Drawing Sheets

F I G . 8
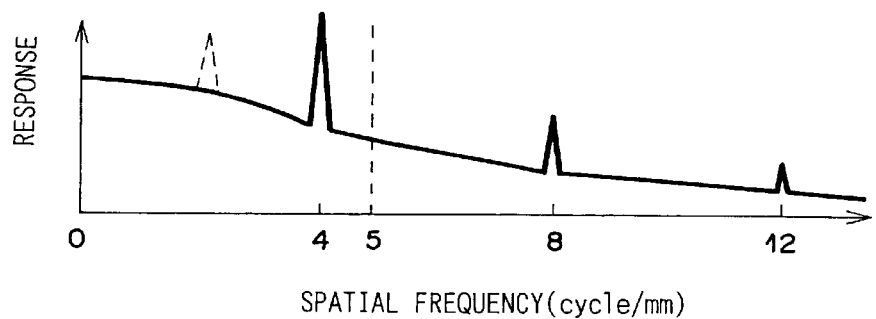

IMAGE SIGNAL GENERATING METHOD, APPARATUS AND PROGRAM

BACKGROUND OF THE INVENTION

1. Field of the Invention

The present invention relates to an image signal generating method and apparatus for generating an image signal by taking an image including a repeated pattern, e.g., a radiation image including a grid pattern corresponding to a grid used when the radiation image is taken. The invention also relates to a program for causing a computer to execute such an image signal generating method.

2. Description of the Prior Art

Radiation recording and reproduction systems have been known from Japanese Unexamined Patent Publication Nos. 55(1980)-12429, 56(1981)-11395, 55(1980)-163472, 56(1981)-164645 and 55(1980)-116340, for example. These known systems use a storage-type phosphor (stimulable phosphor) for the imaging of objects such as a human body. When exposed to radiation such as X-rays, α-rays, β-rays, γ-rays, electron beams and ultraviolet rays, the storage-type phosphor stores part of the radiation. Upon irradiation with a stimulating ray such as visible light, the phosphor emits an amount of stimulated light in proportion to the amount of energy stored. Such known systems with the storage-type phosphor first take a radiation image of an object such as a human body and store it on the storage-type phosphor in the form of a sheet. The storage-type phosphor sheet is then scanned by a stimulating ray such as a laser beam in a main-scan direction while the sheet is transported in a sub-scan direction, thereby producing a stimulated emission of light. The stimulated light emission is photo-electrically read by a reading means such as a photomultiplier to produce an image signal. Based on this image signal, the radiation image of the object can be output as a visible image on a recording medium such as a photosensitive material or on a CRT.

When taking and recording the radiation image of the object on a recording sheet such as the above-described storage-type phosphor sheet, a grid is sometimes disposed between the object and the sheet. The grid is formed of bars of a radiation-impermeable material, such as lead, and a radiation-permeable material, such as aluminum or wood, which are alternately located at small pitches of about 4.0 bars/mm. The grid functions to prevent the sheet from being irradiated by the radiation scattered by the object. Such use of the grid helps to reduce the amount of radiation scattered by the object falling on the sheet, thereby improving the contrast of the radiation image of the object. On the other hand, when the image including an image of the grid is either increased or reduced in size, aliasing occurs due to folding of the frequency characteristics curve, depending on the ratio of enlargement. Furthermore, if such aliasing corresponds with the spatial frequency of the grid pattern, for example, moiré fringes will arise, which will further degrade the quality of the reproduced image.

To counter this problem, it has been proposed to perform filtering processing to remove the spatial frequency components of the grid pattern, so that the moiré or aliasing can be reduced and therefore an image can be obtained that is easy to observe (U.S. Pat. No. 5,028,784, for example). According to this method, the aliasing in the grid pattern caused by folding is removed by filtering processing when the spatial frequency of the grid pattern is higher than a spatial frequency (Nyquist frequency) required for image information.

For example, if the pitch of the grid is 4.0 bars/mm and the Nyquist frequency is 2.5 cycles/mm, aliasing will arise at 1 cycle/mm. Accordingly, the radiation image is first read at smaller sampling intervals than the sampling intervals necessary for image information, and the obtained image data is subjected to a filtering process which removes the spatial frequencies near 4 cycles/mm. Thereafter sampling is effected at sampling intervals required for image information, thereby removing the aliasing.

Since the grid pattern is included in the image signal as a rectangular signal, harmonic components of the grid pattern are contained in a region of high frequencies which are integral multiples of the spatial frequency corresponding to the grid pattern. For example, as shown in FIG. 8, if the grid pattern has a spatial frequency of 4 cycles/mm, a first harmonic component is generated at twice that, i.e., at 8 cycles/mm, and a second harmonic component is generated at three times that grid pattern spatial frequency, i.e., at 12 cycles/mm. When the Nyquist frequency or the spatial frequency necessary for image information is 5 cycles/mm, there will be no moiré in the spatial frequency components corresponding to the grid pattern. However, the first harmonic component folds back at 5 cycles/mm to cause aliasing at 2 cycles/mm, and the second harmonic component folds back at 5 cycles/mm and 0 cycle/mm to cause aliasing at 2 cycles/mm. As a result, a moiré appears at 2 cycles/mm.

According to the above-mentioned method known from U.S. Pat. No. 5,028,784, the harmonic components cannot be removed because of the filtering processing for the removal of the spatial frequency of the grid pattern. As a result, the above-mentioned moiré at 2 cycles/mm cannot be removed. Further, additional aliasing or moiré will be generated if the image containing the aliasing or moiré is increased or reduced in size, thereby adversely affecting the examination of the object. Aliasing due to high-frequency components appears in a relatively low-frequency band within the image. However, such low-frequency band also contains much useful information for the image. Accordingly, an attempt to remove the aliasing may also result in removal of information useful for the image.

SUMMARY OF THE INVENTION

In view of the foregoing problems of the prior art, it is an object of the invention to provide an image signal generating method and apparatus by which a radiation image having no aliasing or moiré can be obtained even if the spatial frequency of the grid pattern is smaller than the spatial frequency necessary for image information, and a program for causing a computer to execute such an image signal generating method.

The image signal generating method according to the present invention comprises the steps of:

obtaining an initial image signal by reading an original image including a repeated pattern repeated with a lower spatial frequency than a maximum spatial frequency of a desired spatial frequency band, wherein the reading is performed at sampling intervals corresponding to a spatial frequency which is not smaller than n (n=a positive number of 2 or more) times the spatial frequency of the repeated pattern;

filtering the initial image signal using a filter for removing spatial frequencies corresponding to harmonics components of the repeated pattern; and obtaining an image signal representing the original image by sampling the thus filtering-processed initial image signal at predetermined sampling intervals corresponding to the maximum spatial frequency or a Nyquist frequency.

In a preferred embodiment of the image signal generating method according to the invention, a sub-sampled signal is obtained by sub-sampling the filtered initial image signal at smaller sampling intervals than the predetermined sampling intervals, and the filtering and sub-sampling of the sub-sampled image signal are repeated until the image signal sampled at the predetermined sampling intervals is obtained.

In a further preferred embodiment of the image signal generating method, a further filtering processing is performed on the image signal to remove the spatial frequency of the repeated pattern.

The maximum spatial frequency of the desired spatial frequency band refers to a spatial frequency necessary for image information, i.e., a Nyquist frequency which is determined by the sampling intervals used in reproducing the image signal representing the original image.

The original image may be a radiation image taken with the use of a grid. In that case, the repeated pattern included in the original image is a grid pattern corresponding to the applied grid. Also in that case, the original image (i.e., the radiation image) is read out from a recording sheet such as a storage-type phosphor sheet. However, the original image is not limited to the radiation image, but may be an image of any other type as far as it includes a repeated pattern such as a stripe pattern or a wire-netting pattern.

When the image signal is obtained from the recording sheet, the recording sheet is scanned by a stimulating beam. With regard to the main-scan direction, the obtained signal tends to be blurred and have poor sharpness due to the emission response delay or the like of the stimulated light, so that the harmonics components do not easily arise. In addition, during the read-out, the signal is obtained as a continuous analog signal as far as the main direction is concerned, so that the harmonics components can be removed by an analog filter. On the other hand, in the sub-scan direction, there is no emission response delay in the stimulated light emission and the harmonics components cannot be removed by an analog filter. As a result, in the sub-scan direction, harmonics components of the repeated pattern (or the grid pattern) are generated and aliasing results due to folding during the sampling. Accordingly, in the case where the original image (or the radiation image) is read out from the recording sheet, the invention has only to effect a filtering processing at least with respect to the sub-scan direction.

The image signal generating apparatus according to the invention comprises:

reading means for obtaining an initial image signal by reading an original image including a repeated pattern repeated with a lower spatial frequency than a maximum spatial frequency of a desired spatial frequency band, wherein the reading is performed at sampling intervals corresponding to a spatial frequency which is not smaller than n (n=a positive number of 2 or more) times the spatial frequency of the repeated pattern;

filtering means for performing a filtering processing on the initial image signal using a filter for removing spatial frequencies corresponding to harmonics components of the repeated pattern; and sampling means for obtaining an image signal representing the original image by sampling the filtering-processed initial image signal at predetermined sampling intervals corresponding to the maximum spatial frequency or a Nyquist frequency.

In a preferred embodiment of the image signal generating apparatus according to the invention, the sampling means obtains a sub-sampled image signal by sub-sampling the filtering-processed initial image signal at smaller sampling intervals than the predetermined sampling intervals, and the filtering processing and sub-sampling of the sub-sampled image signal are repeated until an image signal sampled at the predetermined sampling intervals is obtained.

In another preferred embodiment of the image signal generating signal generating apparatus according to the invention, the filtering means effects a further filtering processing on the image signal to remove the spatial frequency of the repeated pattern.

In addition, a program may be provided for causing a computer to execute the image signal generating method according to the present invention.

Thus, in accordance with the invention, when the spatial frequency of the repeated pattern is lower than the maximum spatial frequency of the desired spatial frequency band, there is first obtained the initial image signal by reading the original image at the sampling intervals that correspond with the spatial frequency which is n or more times the spatial frequency of the repeated pattern. As a result, the initial image signal contains harmonics components of the repeated pattern. The initial image signal is then filtering-processed by a filter, whereby spatial frequencies corresponding to the harmonics components of the repeated pattern are removed. The thus filtering-processed initial image signal is sampled at predetermined sampling intervals corresponding to the maximum spatial frequency or a Nyquist frequency, whereby the image signal representing the original image is obtained. Since the spatial frequencies corresponding to the harmonics components of the repeated pattern are thus removed, it is possible to obtain an image signal for reproducing an image having no aliasing or moiré due to the folding back of the harmonics of the repeated pattern even if the sampling is performed at the predetermined sampling intervals.

When n is relatively large, the harmonics components of the repeated pattern will appear in a plurality of frequency bands. On the other hand, in order to remove those harmonics components caused in the multiple frequency bands, the filter must be increased in size. It is difficult, however, to design such a large-sized filter as required, and also the filtering processing will require a longer period of time. In the present invention, therefore, the need for a large-sized filter is eliminated and the image signal can be obtained by a simple calculation by repeating the filtering processing and sub-sampling until an image signal with predetermined sampling intervals is obtained.

In a preferred embodiment of the apparatus according to the invention, a further filtering processing is performed on the obtained image signal to remove the spatial frequency of the repeated pattern. This prevents the generation of aliasing or moiré caused by the repeated pattern no matter how much the image signal is increased or reduced in size. Thus, it becomes possible to obtain an image signal which can be used to reproduce a high-quality image with a desired ratio of enlargement. In particular, in the case where the original image is a radiation image for medical use, doctors etc. may conduct more accurate diagnosis by obtaining an image signal for reproducing an image free from aliasing or moiré.

BRIEF DESCRIPTION OF THE DRAWINGS

FIG. 8 is a chart for explaining the aliasing due to the harmonics components of the grid pattern.

DESCRIPTION OF THE PREFERRED EMBODIMENTS

A preferred embodiment of the invention is described below with reference to the attached drawings.

Figure 1:
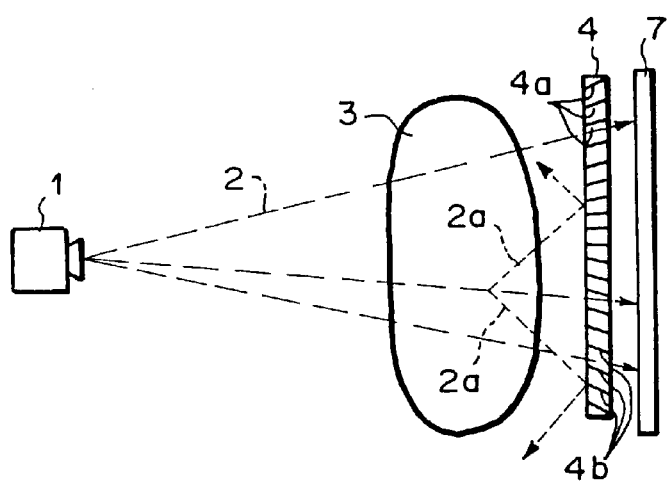
FIG. 1 shows an example of a radiation image taking apparatus.

FIG. 1 schematically shows an example of a radiation image taking apparatus. In the following, a case is described where the original image is a radiation image recorded on a recording sheet and where a storage-type phosphor sheet is used as the recording sheet.

A radiation source 1 emits radiation 2, which travels through an object 3 and a grid 4 and impinges on a storage-type phosphor sheet 7. The grid 4 is formed of an alternate arrangement of bars of lead 4a and aluminum 4b at pitches of 4.0 bars/mm. Radiation 2 is blocked by lead 4a but transmitted by aluminum 4b to irradiate the sheet 7. A grid pattern of 4 bars/mm is thus stored in the sheet 7 together with a radiation image of the object 3. Radiation 2a scattered within the object 3 either impinges on the grid 4 diagonally, and thus blocked, or reflected by the grid 4, and therefore does not impinge on the sheet 7 at all. Thus the sheet 7 stores a sharp radiation image with little irradiation by the scattered radiation. The spatial frequency of the grid pattern is 4 cycles/mm.

Figure 2:
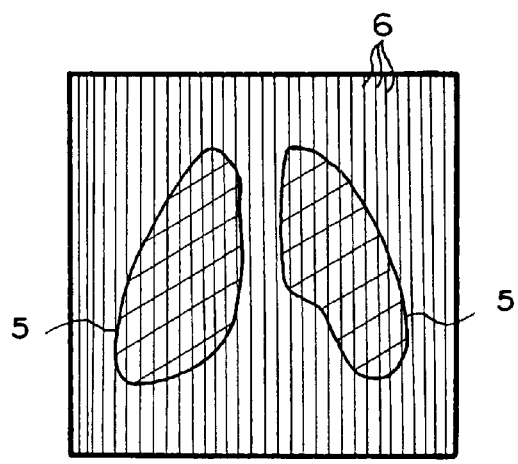
FIG. 2 shows a radiation image taken with the use of a grid.

FIG. 2 shows an illustration of a radiation image taken and stored in storage-type phosphor sheet 7 with the use of the grid. The radiation image consists of an object image (shown shaded by diagonal lines) and a grid pattern (shown shaded by vertical lines) superposed thereon. Thus, there is recorded a radiation image on the sheet 7 consisting of an object image 5 and a grid pattern 6 superposed thereon.

Figure 3:
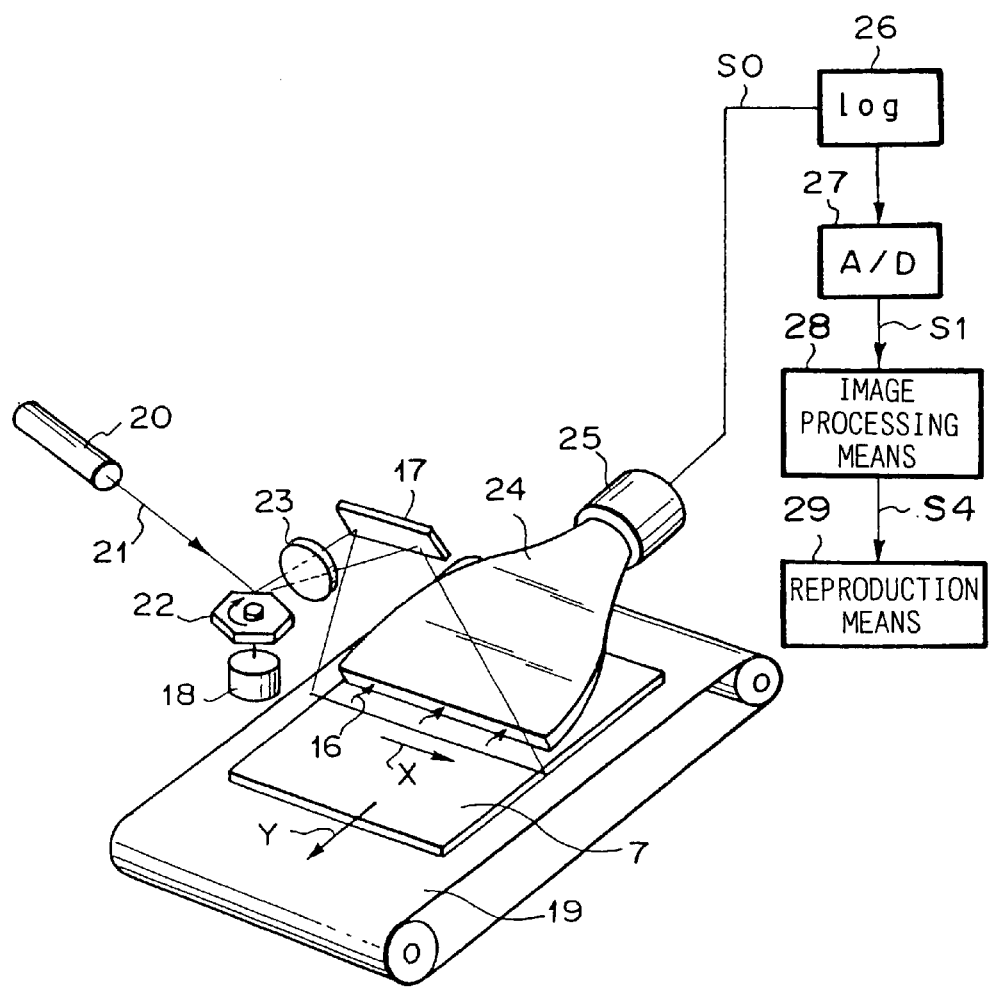
FIG. 3 is a perspective view of an example of a radiation image read-out apparatus.

FIG. 3 shows a perspective view of an example of a radiation image read-out apparatus.

A storage-type phosphor sheet 7 in which the radiation image is recorded is set at a predetermined position and then transported (for the main scan) in a direction indicated by an arrow Y by means of a sheet transporting means 19 such as an endless belt driven by a drive means (not shown). During transportation, the sheet 7 is disposed on the sheet transport means 19 such that the transport direction of the sheet 7 is perpendicular to the grid pattern 6. A laser light source 20 emits a light beam 21 which is deflected by a rotating polygon mirror 22 driven by a motor 18 to rotate at a high speed in a direction indicated by the arrow. The deflected light beam then passes through a converging lens 23 such as an fθ lens, has its optical path changed by a mirror 17 and impinges on the sheet 7 to scan in a main-scan direction indicated by an arrow X which is substantially perpendicular to the sub-scan direction (as indicated by arrow Y). In the present embodiment, the sampling pitch for the reproduction of the radiation image is 10 times/mm (Nyquist frequency 5 cycles/mm), and the sampling pitches for the main- and sub-scan are 40 pixels/mm (Nyquist frequency 20 cycles/mm). Those portions of the sheet 7 where the light beam 21 impinged emit stimulated light 16 with an optical amount in proportion to the radiation image information stored therein. Stimulated light 16 is guided by an optical guide 24 and eventually photoelectrically detected by a photomultiplier tube 25. The photomultiplier tube 25 then converts the stimulated light 16, which represents the radiation image, into an electric signal.

An analog output signal S0 is logarithmically amplified by a log amp 26 and sampled at sampling intervals of 40 pixels/mm by an A/D converter 27, thereby producing a digitized image data S1. Image data S1 is sent to an image processing apparatus 28.

Figure 4A:
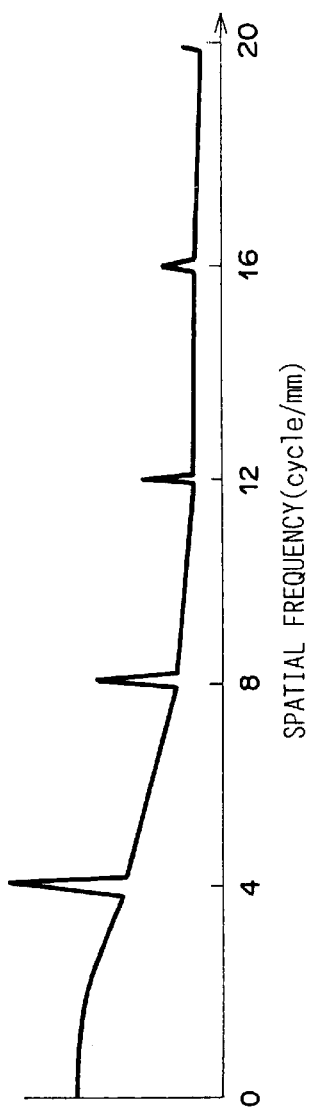
FIGS. 4A to 4C are charts for explaining of the processings performed in the image processing apparatus.

The Nyquist frequency of the image data S1 is 20 cycles/mm, and the spatial frequency of 4 cycles/mm contains the grid pattern information, as shown in FIG. 4A. The harmonics components of the grid pattern are also contained in a region of high frequencies which are integral multiples of the spatial frequency of the grid pattern. Specifically, information of a first harmonic component, a second harmonic component, a third harmonic component and a fourth harmonic component are contained at 8 cycles/mm, 12 cycles/mm, 16 cycles/mm and 20 cycles/mm, respectively. The harmonics components of the grid pattern are removed by image processing apparatus 28 through the following processings performed on the image data S1.

Figure 5:
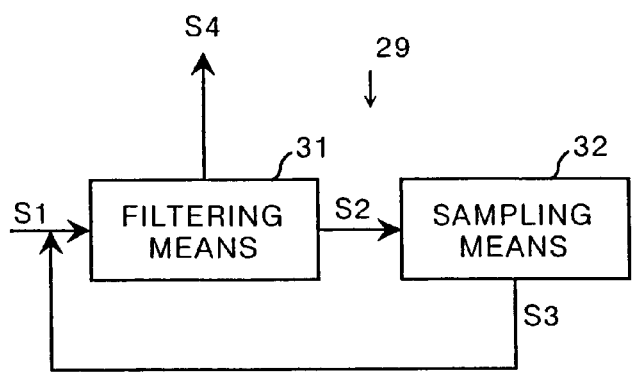
FIG. 5 shows a block diagram of the configuration of the image processing apparatus.

FIG. 5 shows a block diagram of the configuration of the image processing apparatus 28. As shown, the image processing apparatus 28 comprises filtering means 31 for carrying out a filtering processing on image data S1 to thereby obtain a filtering-processed image data S2, and sampling means 32 for sub-sampling image data S2 such that the number of pixels in the main and sub directions are reduced by half in order to make the size of image data S2 one half the size of the image represented by image data S1, thereby producing a sampling-processed image data S3.

Filtering means 31 performs filtering processing image data S1 using a filter with such characteristics that its response is substantially zero at those high-frequency components (13.3 cycles/mm or more) that are more than two thirds the Nyquist frequency (20 cycles/mm) of image data S1. The filter coefficients of this filter are shown below. The number of taps of the filter is 15 (15th order).

−1, 1, 4, −3, −14, 0, 43, 68, 43, 0, −14, −3, 4, 1, −1

Figure 6:
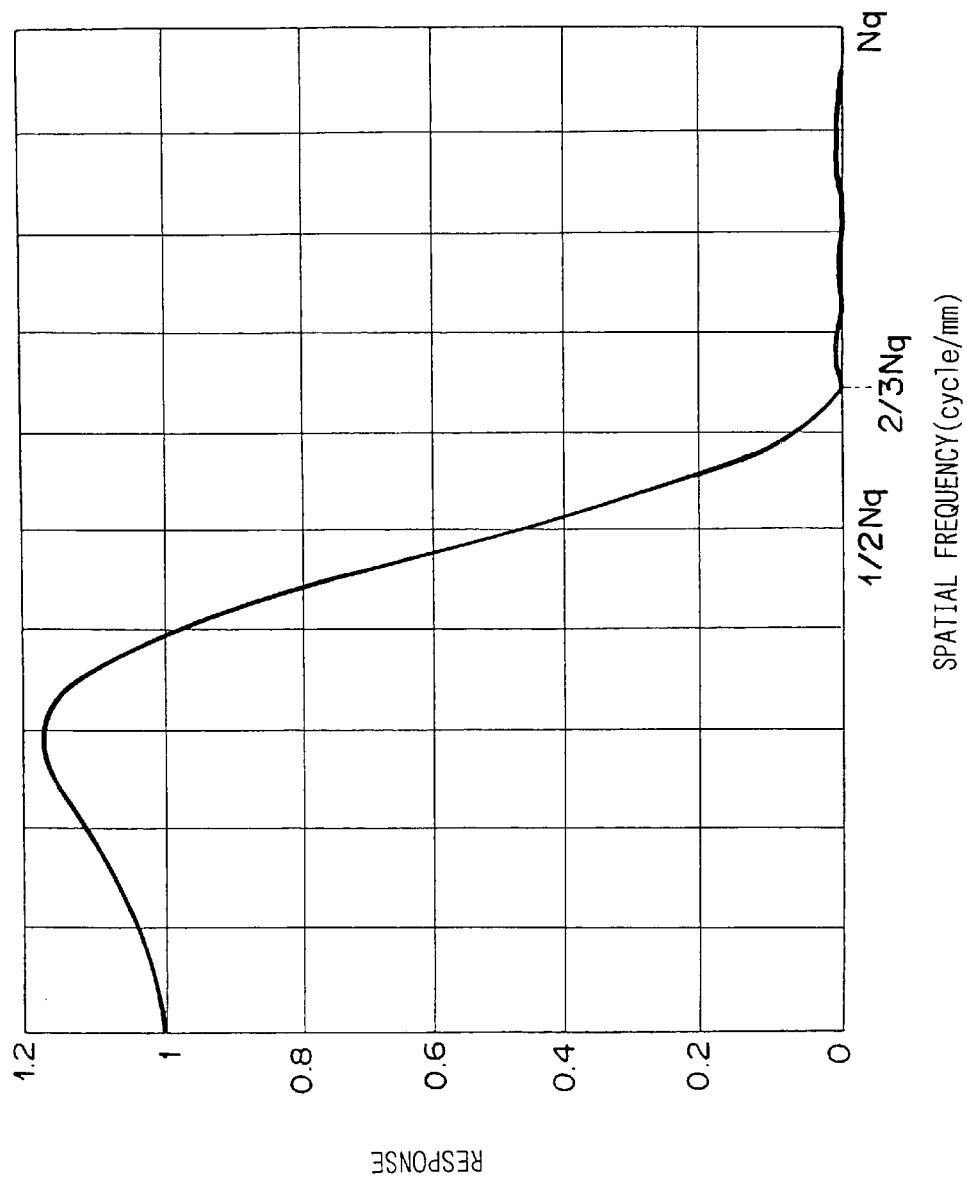
FIG. 6 is a chart showing the characteristics of the filter.

The filter characteristics of the filter are shown in FIG. 6. As shown, the filter reduces the response of those high-frequency components that are two thirds or more of the Nyquist frequency Nq down to 5% or less.

Image data S2, which was obtained by performing the filtering processing on the image data S1 using the above filter, has information of the third and fourth harmonics components of the grid pattern that were contained at 16 cycles/mm and 20 cycles/mm removed, and has information of the second harmonic component contained at 12 cycles/mm reduced.

Figure 4B:
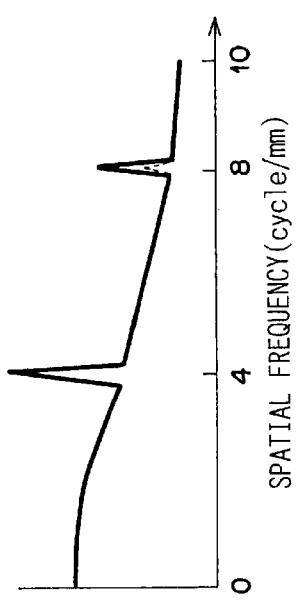

Sampling means 32 sub-samples image data S2 such that the number of pixels in both the main and sub directions is reduced by half, thereby producing image data S3 which has been sample-processed. The frequency characteristics of the image data S3 are shown in FIG. 4B. As shown, the Nyquist frequency of the image data S3 is made 10 cycles/mm by the sub-sampling. The information of the 12-cycles/mm harmonic component left somewhat by the filtering processing is folded back at 10 cycles/mm, causing aliasing to appear at 8 cycles/mm.

Thereafter image data S3 is input to filtering means 31 as new image data S1. Filtering means 31 performs a filtering processing on image data S1 using a filter similar to the one mentioned above having such characteristics that the response at those high-frequency components (6.7 cycles/ mm or more) that are at least two thirds the Nyquist frequency (10 cycles/mm) becomes substantially zero. Resultant image data S2 has information of the first harmonic component of the grid pattern contained at 8 cycles/ mm removed.

Figure 4C:
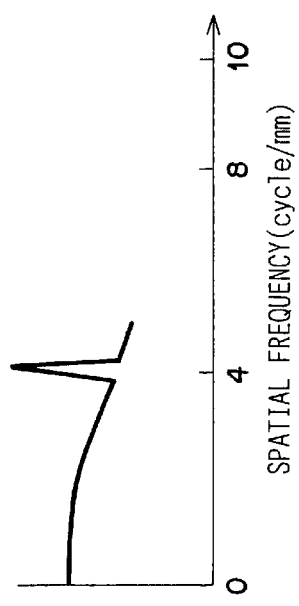

Sampling means 32 performs sub-sampling processing on the image data S2 in the same manner as mentioned above, thereby producing sampling-processed image data S3. The frequency characteristics of the newly obtained image data S3 are shown in FIG. 4C. As shown, the Nyquist frequency of the image data S3 is the same as for reproduction, i.e., 5 cycles/mm, where information of the harmonic components of the grid pattern and aliasing due to the harmonics components are removed.

Image data S3 obtained by the two filtering processings and the two sub-sampling processings is again input to filtering means 31 as new image data S1, where the filtering processing is performed using the same filter as mentioned above to produce image data S4 which has been processed for the last time. The image data S4 has a response of substantially zero at those high-frequency components (3.3 cycles/mm or more) that are two thirds the Nyquist frequency (5 cycles/mm), and therefore has the information of the grid pattern removed.

Thus obtained image data S4 is reproduced by a reproduction means 29 such as a monitor or printer in the form of a visual image.

Figure 7:
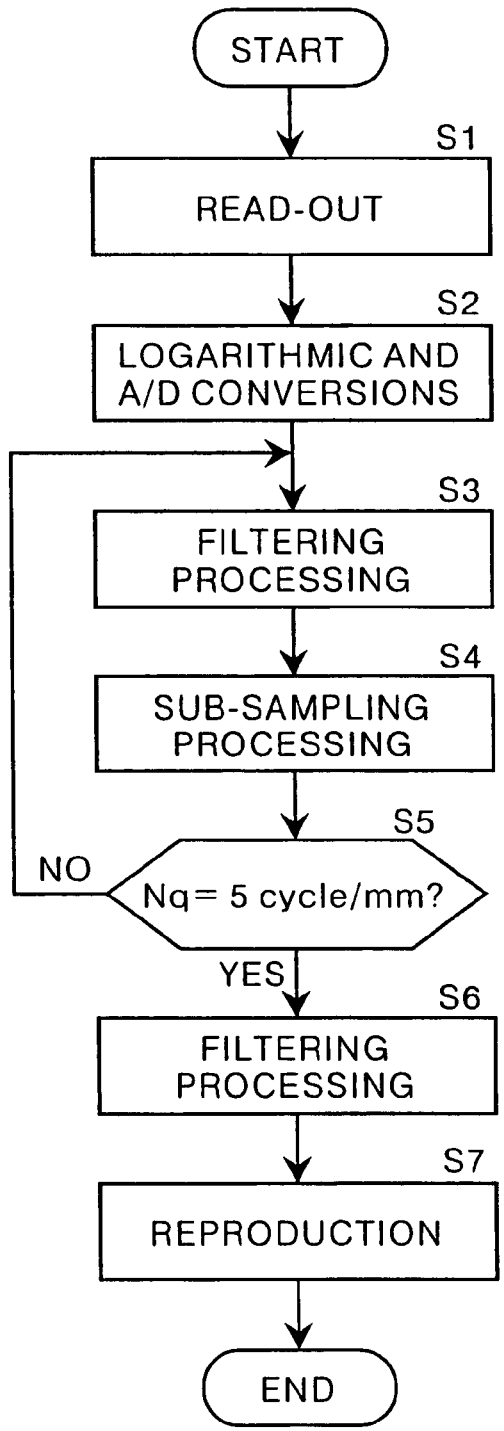
FIG. 7 is a flowchart of the operation of an embodiment of the invention.

The operation of the embodiment is described with reference to FIG. 7 showing a flowchart of the operation. Initially, the radiation image is read from the storage-type phosphor sheet, where the image has been stored, to obtain image data S0 (step S1). Obtained image data S0 is logarithmically amplified by log amplifier 26, and then digitized by an A/D converter 27 (step S2), thereby producing digital image data S1. The image data S1 is input to image processing apparatus 28, where a filtering processing is performed to obtain filtering-processed image data S2 (step S3). Image data S2 is sub-sampled by sampling means 32 to produce sampling-processed image data S3 (step S4). Thereafter it is determined whether or not the image data S3 has the Nyquist frequency (Nq=5 cycles/mm) for the reproduction following the sub-sampling processing (step S5). If the answer is negative in step S5, the procedure goes back to step S3 to repeat the filtering and sub-sampling processings by using the image data S3 as new image data S1. On the other hand, if the answer in step S5 is positive, filtering means 31 performs a filtering processing on the obtained image data S3 (step S6), whereby final-processed image data S4 is obtained. Image data S4 is reproduced by reproduction means 29 as a visible image (step S7), and the entire procedure ends.

Thus, in accordance with the embodiment, the spatial frequencies corresponding to the harmonics components of the grid are removed prior to the sampling at the sampling intervals necessary during reproduction. Accordingly, it is possible to image data S4 based on which a high-quality radiation image can be reproduced that has no aliasing or moiré caused by the folding of the harmonics components of the grid pattern.

Further, since the filtering and sampling processings are repeated on image data S1 until such sampling intervals are obtained that are required for reproduction, there is no need to provide a relatively large-sized filter, making it possible to obtain image data S4 by a simple calculation.

Due to the filtering processing to remove the spatial frequency of the grid pattern, there arises no aliasing or moiré due to the grid pattern no matter how much image data S4 is increased or reduced in size. Accordingly, there can be obtained a high-quality radiation image with a desired ratio of enlargement, which enables the object such as a human body to be examined accurately.

While in the embodiment the filtering processing is performed using the filter having such characteristics as shown in FIG. 5, this is not to be taken as limiting the invention. Any filter can be utilized as long as it is capable of removing the harmonics components of the grid pattern.

Furthermore, while in the embodiment the filtering processing is repeated by using the filter as shown in FIG. 5, the filtering processing may be effected by using a filter that can remove all of the harmonics components from the image data S1 at once.

In addition, although the filter processing in the above-described embodiment is performed on the image data obtained by reading the radiation image including the grid pattern from the storage-type phosphor sheet, it may be performed on an image of any other type as far as the image includes a repeated pattern. For example, the filtering process may also be performed in the same way as described above on an image of a person wearing a stripe shirt or an image including an image of wire netting, in order to obtain image data for reproducing a high-quality image free from aliasing or moiré due to folding back of the harmonics of the repeated pattern.

What is claimed is:

1. An image signal generating method comprising the steps of:

obtaining an initial image signal by reading an original image including a repeated pattern repeated with a lower spatial frequency than a maximum spatial frequency of a desired spatial frequency band, wherein the reading is performed at sampling intervals corresponding to a spatial frequency which is not smaller than n (n=a positive number of 2 or more) times the spatial frequency of the repeated pattern;

filtering the initial image signal using a filter for removing spatial frequencies corresponding to harmonics components of the repeated pattern; and obtaining an image signal representing the original image by sampling the thus filtering-processed initial image signal at predetermined sampling intervals corresponding to the maximum spatial frequency or a Nyquist frequency.

2. An image signal generating method according to claim 1, further comprising the steps of:

obtaining a sub-sampled image signal by sub-sampling the filtering-processed initial image signal at smaller sampling intervals than the predetermined sampling intervals; and repeating the filtering processing and sub-sampling of the sub-sampled image signal until there an image signal sampled at the predetermined sampling intervals is obtained.

3. An image signal generating method according to claim 1 or 2, wherein further filtering processing is performed on the image signal to remove the spatial frequency of the repeated pattern.

4. An image signal generating apparatus comprising:

reading means for obtaining an initial image signal by reading an original image including a repeated pattern repeated with a lower spatial frequency than a maximum spatial frequency of a desired spatial frequency band, wherein the reading is performed at sampling intervals corresponding to a spatial frequency which is not smaller than n (n=a positive number of 2 or more) times the spatial frequency of the repeated pattern;

filtering means for performing a filtering processing on the initial image signal using a filter for removing spatial frequencies corresponding to harmonics components of the repeated pattern; and sampling means for obtaining an image signal representing the original image by sampling the filtering-processed initial image signal at predetermined sampling intervals corresponding to the maximum spatial frequency or a Nyquist frequency.

5. An image signal generating apparatus according to claim 4, wherein the sampling means obtains a sub-sampled image signal by sub-sampling the filtering-processed image signal at smaller sampling intervals than the predetermined sampling intervals, and the filtering processing and sub-sampling of the sub-sampled image signal are repeated until the image signal sampled at the predetermined sampling intervals is obtained.

6. An image signal generating apparatus according to claim 4 or 5, wherein the filtering means performs a further filtering processing on the image signal to remove the spatial frequency of the repeated pattern.

7. A program for causing a computer to execute the procedures of:

obtaining an initial image signal by reading an original image including a repeated pattern repeated with a lower spatial frequency than a maximum spatial frequency of a desired spatial frequency band, wherein the reading is performed at sampling intervals corresponding to a spatial frequency which is not smaller than n (n=a positive number of 2 or more) times the spatial frequency of the repeated pattern;

filtering the initial image signal using a filter for removing spatial frequencies corresponding to harmonics components of the repeated pattern; and obtaining an image signal representing the original image by sampling the thus filtering-processed initial image signal at predetermined sampling intervals corresponding to the maximum spatial frequency or a Nyquist frequency.

8. A program according to claim 7, wherein the sampling procedure produces a sub-sampled image signal by sub-sampling the filtering-processed initial image signal at smaller sampling intervals than the predetermined sampling intervals, the program further comprising a procedure of repeating the filtering processing and sub-sampling of the sub-sampling image signal until an image signal sampled at the predetermined sampling intervals is obtained.

9. A program according to claim 7 or 8, the program comprising a procedure of performing further filtering processing on the image signal to remove the spatial frequency of the repeated pattern.

* * * * *